(12) United States Patent
Hastings et al.

(10) Patent No.: US 8,718,751 B2
(45) Date of Patent: May 6, 2014

(54) MONITORING SYSTEM FOR SLEEP DISORDERED BREATHING

(75) Inventors: David F. Hastings, Lake Oswego, OR (US); Xin Good, Tigard, OR (US); Hannes Kraetschmer, West Linn, OR (US); Dirk Muessig, West Linn, OR (US)

(73) Assignee: BIOTRONIK CRM Patent AG (CH)

( * ) Notice: Subject to any disclaimer, the term of this patent is extended or adjusted under 35 U.S.C. 154(b) by 1758 days.

(21) Appl. No.: 11/746,156

(22) Filed: May 9, 2007

(65) Prior Publication Data

US 2007/0265539 A1 Nov. 15, 2007

Related U.S. Application Data

(60) Provisional application No. 60/747,211, filed on May 15, 2006.

(51) Int. Cl.
*A61B 5/08* (2006.01)
*A61B 5/04* (2006.01)
*A61B 5/053* (2006.01)
*A61B 5/085* (2006.01)

(52) U.S. Cl.
USPC .......................................... 600/513; 600/484

(58) Field of Classification Search
USPC ................................ 607/19, 20; 600/484, 513
See application file for complete search history.

(56) References Cited

U.S. PATENT DOCUMENTS

| | | | |
|---|---|---|---|
| 6,641,542 B2 | 11/2003 | Cho et al. | |
| 6,881,192 B1 | 4/2005 | Park | |
| 7,155,278 B2 | 12/2006 | King et al. | |
| 7,371,220 B1 * | 5/2008 | Koh et al. | 600/529 |
| 2002/0193697 A1 | 12/2002 | Cho et al. | |
| 2004/0111040 A1 * | 6/2004 | Ni et al. | 600/534 |
| 2004/0210261 A1 | 10/2004 | King et al. | |

FOREIGN PATENT DOCUMENTS

WO   WO 2004/112606 A   12/2004

OTHER PUBLICATIONS

De Souza, W.M. et al, "Variability of thoracic impedance cardiograms in man," *Medical & Biological Engineering & Computing*, 1981, vol. 19, No. 4, pp. 411-415.

Search Report of the European Patent Office for Application Serial No. 07008999.0 in the name of BIOTRONIK CRM Patent AG, Sep. 6, 2007.

* cited by examiner

*Primary Examiner* — Tammie K Heller
(74) *Attorney, Agent, or Firm* — Craig A. Fieschko, Esq.; DeWitt Ross & Stevens S.C.

(57) ABSTRACT

A heart monitoring system comprises a ventricular sensing stage sensing excitation or contraction of ventricular myocardium, an activity sensor unit determining a signal reflecting a patient's physical activity, a ventricular impedance or conductance measuring module, said modules comprising a current source unit adapted to provide a sub-threshold excitation current to the myocardium and comprising an impedance or conductance measurement unit for measuring the resulting voltage on said electrode at the myocardium, a signal generator module, a filter module, a memory, a control unit adapted to derive single measures |ΣZ| of magnitude of impedance or conductance change over a preset sample time interval, determine the variability TARVI in the impedance or conductance change, compare this variability and the activity sensor output signal with a threshold and recent history, determine if sleep disturbed breathing (SDB) is present, and log the SDB episode in the memory device.

34 Claims, 5 Drawing Sheets

MONITORING SYSTEM FOR SLEEP DISORDERED BREATHING

CROSS-REFERENCE TO RELATED APPLICATIONS

This application claims priority under 35 USC §119(e) to U.S. Provisional Patent Application 60/747,211 filed 15 May 2006, the entirety of which is incorporated by reference herein.

BACKGROUND OF THE INVENTION

The invention relates to a monitoring system for monitoring sleep disordered breathing (SDB).

Sleep disordered breathing (SDB) adversely affects the systemic circulation (hypertension), the pulmonary circulation (pulmonary hypertension) and the myocardium (systolic and diastolic heart failure). Continual management of the SDB disorder is part of the overall management strategy for cardiac disease. The SDB burden is an under observed disorder and rarely quantified, because apnea and hypopnea episodes occur at night and out of the clinical setting.

Therefore there is a need for an automatic monitor of the SDB burden that would permit the clinician to manage the SDB risk factor.

Known solutions monitor the intra-thoracic impedance as a proxy for successful ventilation, (respiratory frequency and tidal volume). The clinical impact of the proxy impedance measurement with respect to the patient's cardiovascular system is not measured and can only be inferred by using epidemiological clinical studies.

Three and four intra-thoracic electrode measurements contain thoracic information, e.g. breathing effort and minute ventilation, as well as heart specific information.

Intra-thoracic impedance measurements often cannot detect obstructive apnea, due to the persistence of thoracic and abdominal breathing effort.

SUMMARY OF THE INVENTION

It is an object of the invention to provide an automatic monitor of the SDB burden providing reliable information on SDB burden and that can be implemented without excessive effort.

According to the invention this object is achieved by a heart monitoring system for monitoring at least a ventricle of a heart.

The heart monitoring system comprises:
a ventricular sensing stage connected or being connectable to an electrode for picking up electric potentials inside at least a ventricle of a heart, said sensing stage being adapted to sense an excitation or a contraction of ventricular myocardium,
an activity sensor unit inside a lead or the device which is capable of determining an activity signal reflecting a patient's physical activity,
a ventricular impedance or conductance measuring module connected or being connectable to an electrode measuring the resistance of at least a ventricle of a heart, said impedance or conductance measuring module comprising a current source unit adapted to provide a sub-threshold excitation current to the myocardium and comprising an impedance or conductance measurement unit adapted to measure the resulting voltage on said electrode at the myocardium,
a signal generator module connected to the current source unit and the voltage measurement unit to construct the intra-cardiac impedance or conductance signal reflecting the time course of the impedance or conductance measurement unit's output signal and its derivative,
a filter module to filter the intra-cardiac impedance signal,
a memory for storing a history of intra-cardiac impedance values, and
a control unit that is connected to said memory, said sensing stage, said activity sensor and to said impedance or conductance measuring module.

The control unit is adapted to
derive single measures |ΣZ| of magnitude of impedance or conductance change over a preset sample time interval,
determine the Total Active Right Ventricular Impedance variability TARVI, in the impedance or conductance change over a small number, e.g. 8, of cardiac cycles,
compare the variability in the impedance or conductance change with a threshold and recent history,
compare the activity sensor output signal with a threshold and recent history data stored in said memory,
determine if sleep disturbed breathing (SDB) is present, and
log the SDB episode in the memory device.

In addition to measuring a proxy for minute ventilation according to the prior art, the monitoring system according to the invention measures one or more attributes of ventricular systolic and/or diastolic function, and differentiates obstructive apnea from successful ventilation. Successful and unsuccessful breathing effort influence right ventricular filling, thus permitting the correlation of all classes of SDB with cardiac function. Unexplained excess activation of the cardiovascular system associated with SDB is the source of the SDB burden. The device may report trends in the SDB burden during routine follow-up. Optionally the device may report the SDB burden, via remote monitoring, to a patient management service.

It has been found that
the indirect effect of apnea on cardiac function can be used to detect central, mixed and obstructive apnea episodes with good sensitivities.
the apnea episode detection may be used to automatically intervene to reduce the net SDB burden.
the apnea episode rate may be used to trend the apnea burden upon the cardiovascular system.

The invention provides or allows for the following advantages over the prior art:
A more specific, more timely, and more cost effect indication of the SDB severity.
Improved patient management.
Reduced frequency of hospitalisation and clinical visits.
Improved long-term heart failure morbidity.
Prolongation of life.
Improved quality of life.
Decreased cost of disease management.

Variations and preferred embodiments of the monitoring system include:

Intracardiac impedance measurements provide measures of cardiac systolic and diastolic function. Intra-cardiac impedance may be measured using one or many intra-cardiac electrodes. Unipolar intracardiac impedance measurements provide the simplest method for measuring cardiac systolic and diastolic function. Impedance measurements focused outside the heart provides a measure of successful respiratory action (minute ventilation), and accelerometer provides evidence of corporeal motion.

The information from these intra-cardiac and extra cardiac sensors plus other sensors can be integrated to create the index of SDB burden. In particular, the monitoring system may be adapted to identify sequences of SDB episodes and measure the sequence duration. Further, the monitoring system may be adapted to accumulate the daily total duration of SDB sequences, the SDB burden. A telemetry unit provides a communication channel to a central service center.

According to a preferred embodiment, the device incorporating the monitoring system provides a means for automatic intervention to reduce the SDB burden. In that respect, the monitoring system may be adapted to modify a heart rate to reduce the cardiac excitability. Alternatively, the monitoring system may be adapted to modify a cardiac afferent neural signal to the brain to further reduce the cardiac excitability. Preferably, the monitoring system is adapted to stimulate the inhibitory nerves targeting the heart to reduce the cardiac excitability.

The invention may be used as a stand-alone monitor of SDB, or it may be included as a component of other therapies including implanted cardiac devices: pacemakers, defibrillators, and ventricular assist devices.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
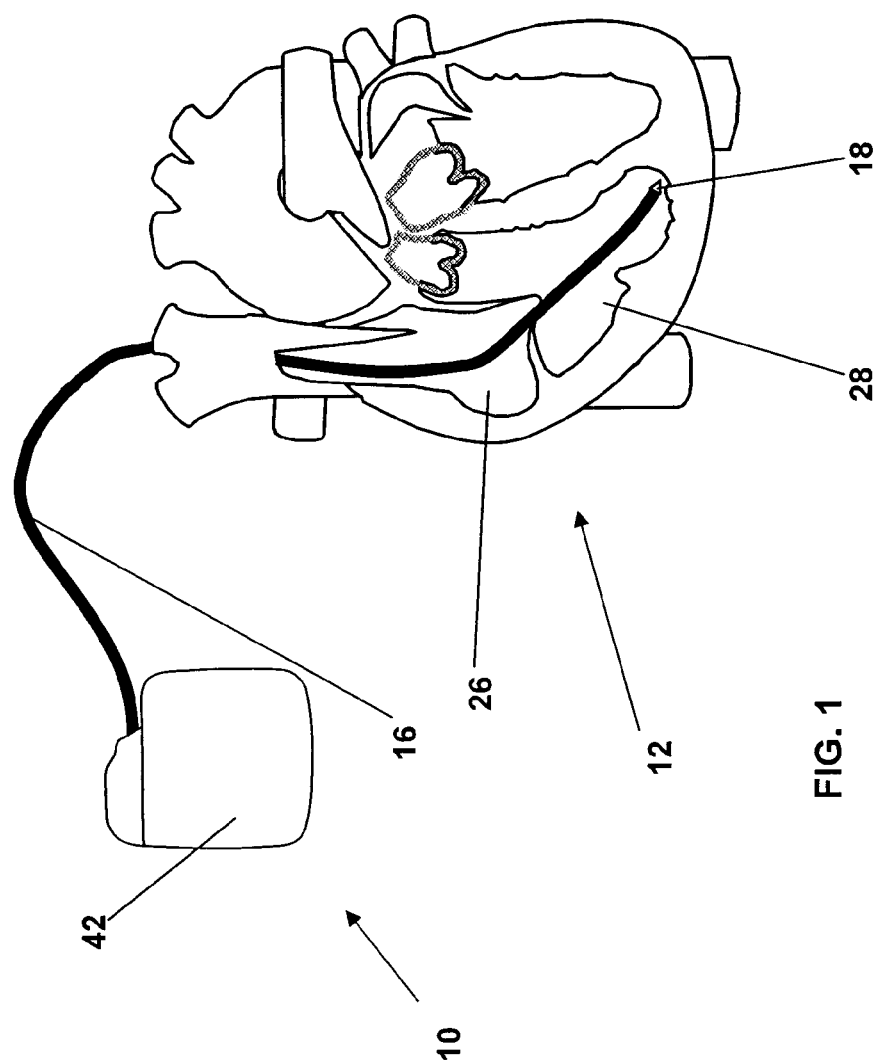
FIG. 1 shows a configuration for an exemplary Sleep Disturbed Breathing (SDB) monitor.

FIG. 1 shows an exemplary configuration for implementing the monitoring for SDB burden with an implantable medical device.

As shown in FIG. 1, the implementation of the SDB monitor with an implantable medical device 10 requires at least one ventricular electrode affixed to the right or left ventricular chamber, a method to measure at least the intrinsic ventricular activation, a method to measure the intra-cardiac impedance.

In the preferred embodiment as shown in FIG. 1, impedance is measured by injecting a current between a right ventricular tip electrode 18 and an electrically conducting case 42 of the implantable medical device 10. The voltage difference is measured between the same two electrodes 18 and 42. For geometric reasons, 75% or more of the impedance is due to the lead/myocardium interface and ventricular volume. There is a small component due to the intra-thoracic impedance (minute ventilation), which is removed by measuring the derivative of the impedance measurement signal.

Figure 2:
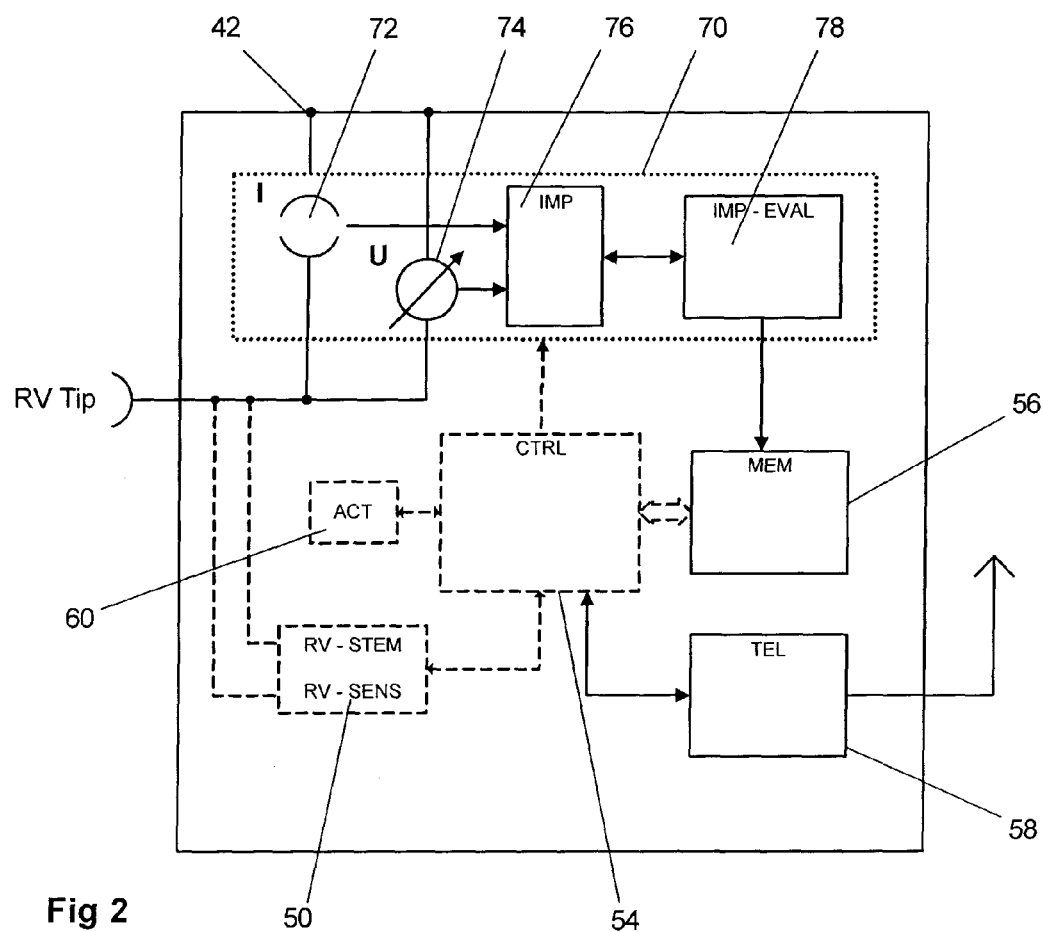
FIG. 2 is a schematic diagram of an exemplary configuration for the monitor.

FIG. 2 shows an arrangement usable for the monitor of FIG. 1. As shown in FIG. 2, the device contains modules to sense and pace a ventricular chamber of the heart. The device contains modules to perform the impedance measurement 70: The device contains a module to inject the excitation current 72, to measure the resulting voltage 74, to determine the impedance 76 and evaluate the impedance change (derivative) 78, and a memory device 56 to store the systolic and diastolic impedance measurements. The device contains a controller 54 to perform algorithmic data processing and to take the indicate actions. The device contains a module 58 to communicate the SDB burden via telemetry to the clinic.

Figure 3:
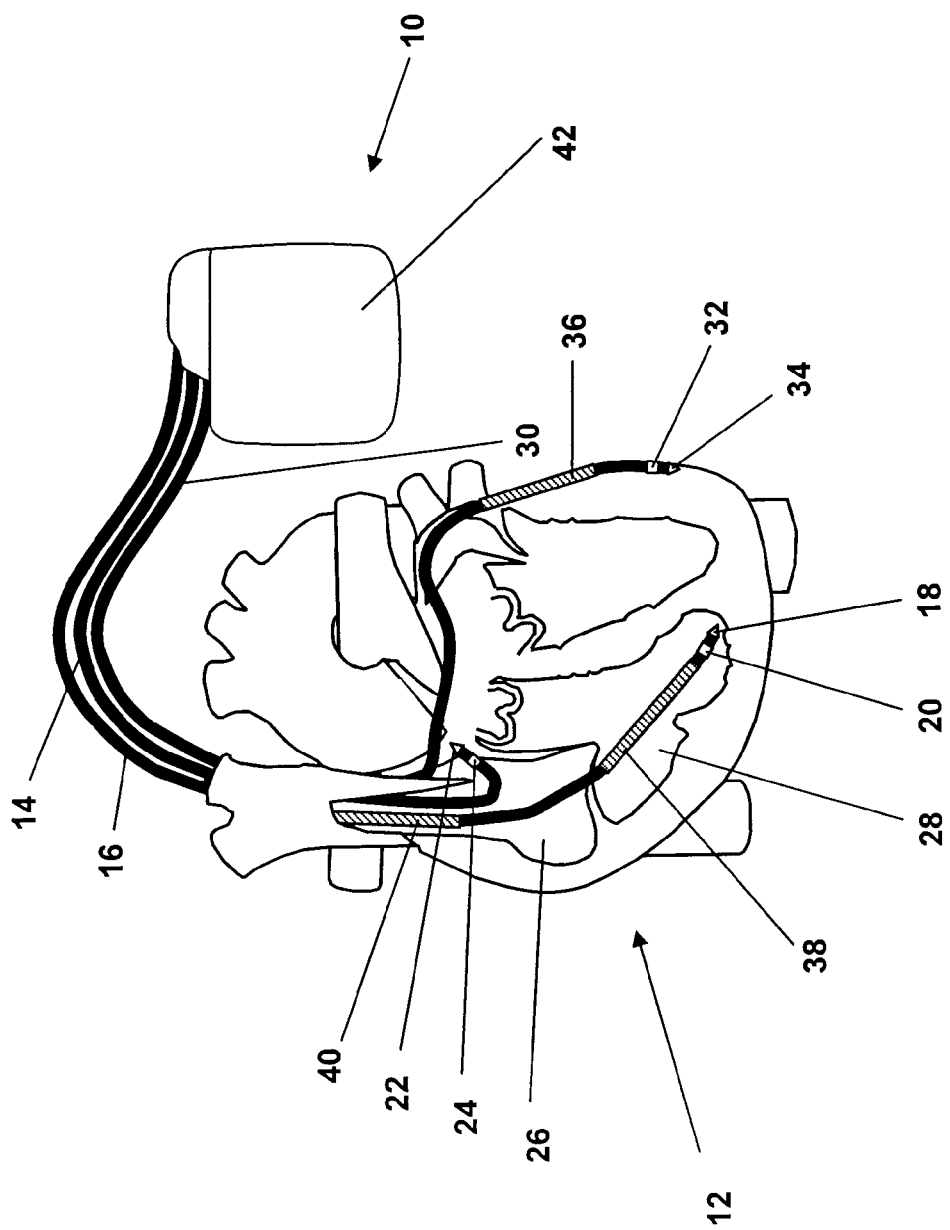
FIG. 3 shows a three chamber bi-ventricular implantable cardioverter/defibrillator (ICD).

In FIG. 3 the implantable medical device is a three chamber biventricular pacemaker and cardioverter/defibrillator 10 that is connected to pacing/sensing leads placed in a heart.

As shown in FIG. 3, the preferred embodiment is to couple the disclosed technology with a implantable bi-ventricular defibrillator.

The implantable medical device 10 is electrically coupled to heart 12 by way of leads 14, 16 and 30.

Lead 14 is a right atrial electrode lead that has a pair of right atrial electrodes 22 and 24 that are in contact with the right atria 26 of the heart 12.

Lead 16 is a right ventricular electrode lead that has a pair of ventricular stimulation an sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32 and a left ventricular tip electrode LV TIP 34. Further, a left ventricular defibrillation shock coil 36 is arranged on lead 30.

Implantable medical device 10 has a case 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

Figure 4:
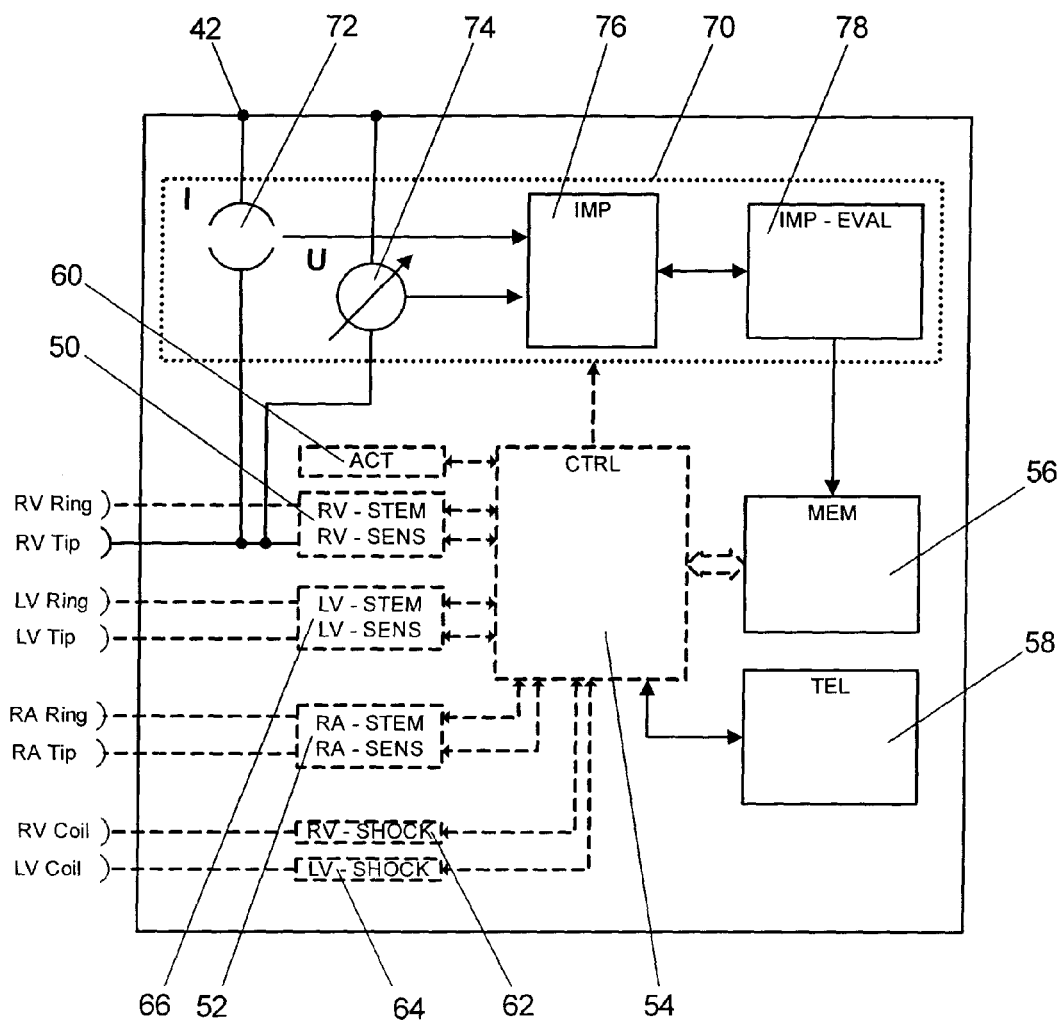
FIG. 4 is a schematic diagram of the device modules of the ICD of FIG. 3.

Referring to FIG. 4 a simplified block diagram of a three chamber pacemaker or cardioverter/defibrillator 10 is illustrated. During operation of the pacemaker leads 14 and 16 are connected to respective output/input terminals of pacemaker 10 as indicated in FIG. 3, and referring to FIG. 4, they carry stimulating pulses to the tip electrodes 22 and 18 from an atrial stimulation pulse generator 52 and ventricular pulse generators 50 and 66, respectively. Further, electrical signals from the atrium are carried from the electrode pair 18 and 20, through the lead 14, to the input terminal of an atrial channel sensing stage 52; and electrical signals from the ventricles are carried from the electrode pair 22/24 and electrode pair 32/34 through the leads 16 and 30 respectively, to the input terminals of the ventricular sensing stages 50 and 66.

Controlling the dual chamber pacemaker 10 is a control unit CTRL 54 that is connected to atrial stimulation and sensing stages 52 and to ventricular stimulation and sensing stages 50 and 66. Control unit CTRL 54 receives the output signals from the atrial sensing stage 52 and from the ventricular sensing stages 50 and 66. The output signals of sensing stages 52, 50 and 66 are generated each time that a P-wave representing an intrinsic atrial event or an R-wave representing an intrinsic ventricular event, respectively, is sensed within the heart 12. An As-signal is generated when the atrial sensing stage 52 detects a P-wave, and a Vs-signal is generated when the ventricular sensing stage 50 or 66 detect an R-wave.

Control unit CTRL 54 also generates trigger signals that are sent to the atrial stimulation pulse generator 52 and the ventricular stimulation pulse generators 50 and 66, respectively. These trigger signals are generated each time that a stimulation pulse is to be generated by the respective pulse generator. The atrial trigger signal is referred to simply as the "A-pulse", and the ventricular trigger signals are referred to as the "V-pulse".

During the time that either an atrial stimulation pulse or ventricular stimulation pulse is being delivered to the heart, the corresponding sensing stages in 52, 50 and 66 are typically disabled by way of a blanking signal presented to these amplifiers from the control unit CTRL 54, respectively. This blanking action prevents the sensing stages 52, 50 and 66 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Furthermore, atrial sense events As recorded shortly after delivery of a ventricular stimulation pulses during a preset time interval called the post ventricular atrial refractory period (PVARP) are generally recorded as atrial refractory sense events Ars, but are ignored.

Control unit CTRL 54 comprises circuitry for timing ventricular and/or atrial stimulation pulses according to an adequate stimulation rate that can be adapted to a patient's hemody-namic need as pointed out below.

Still referring to FIG. 4, the pacer 10 includes a memory circuit MEM 56 that is coupled to the control unit CTRL 54 over a suitable data/address bus ADR. This memory circuit MEM 56 allows certain control parameters, used by the control unit CTRL 54 in controlling the operation of the pacemaker 10, to be programmably stored and modified, as required, in order to customize the pacemaker's operation to suit the needs of a particular patient. Such data includes the basic timing intervals used during operation of the pacemaker 10 and AV delay values and hysteresis AV delay values in particular.

Further, data sensed during the operation of the pacemaker may be stored in the memory MEM 56 for later retrieval and analysis.

A telemetry circuit TEL 58 is further included in the pacemaker 10. This telemetry circuit TEL 46 is connected to the control unit CTRL 54 by way of a suitable command/data bus. Telemetry circuit TEL 58 allows for wireless data exchange between the pacemaker 10 and some remote programming or analyzing device which can be part of a centralized service provider serving multiple pacemakers.

The implantable medical device 10 in FIG. 3 is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage and the stimulation pulse generator 52 and corresponding portions of the control unit CTRL 54, are commonly referred to as the atrial channel. Similarly, those portions of the pacemaker 10 that interface with the right ventricle 28, e.g., the lead 16, the R-wave sensing stage and, the right ventricular stimulation pulse generator 50, and corresponding portions of the control unit CTRL 54, are commonly referred to as the right ventricular channel.

In order to be able to detect periods of physical activity of a patient indicating that the patient is awake and in order to allow rate adaptive pacing in a DDDR or a DDIR mode, the pacemaker 10 further includes a physiological sensor ACT 60 that is connected to the control unit CTRL 40 of the pacemaker 10. While this sensor ACT 60 is illustrated in FIG. 2 as being included within the pacemaker 10, it is to be understood that the sensor may also be external to the pacemaker 10, yet still be implanted within or carried by the patient. A common type of sensor is an accelerometer, such as a piezoelectric crystal, mounted to the case of the pacemaker. Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to physical activity of a patient can be used. Such sensors are commonly used with "rateresponsive" pacemakers in order to adjust the rate of the pacemaker in a manner that tracks the physiological needs of the patient.

The control unit CTRL 54 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporal placement as shown in FIG. 1 or 3. In order to allow for a plurality of impedance measurement electrode configurations, preferably some means of switching is provided between the constant current source 72 and the electrode terminals of the implantable medical device 10. The switch is not shown in FIG. 4. Rather, a particular impedance measurement configuration is shown as an example.

Figure 5:
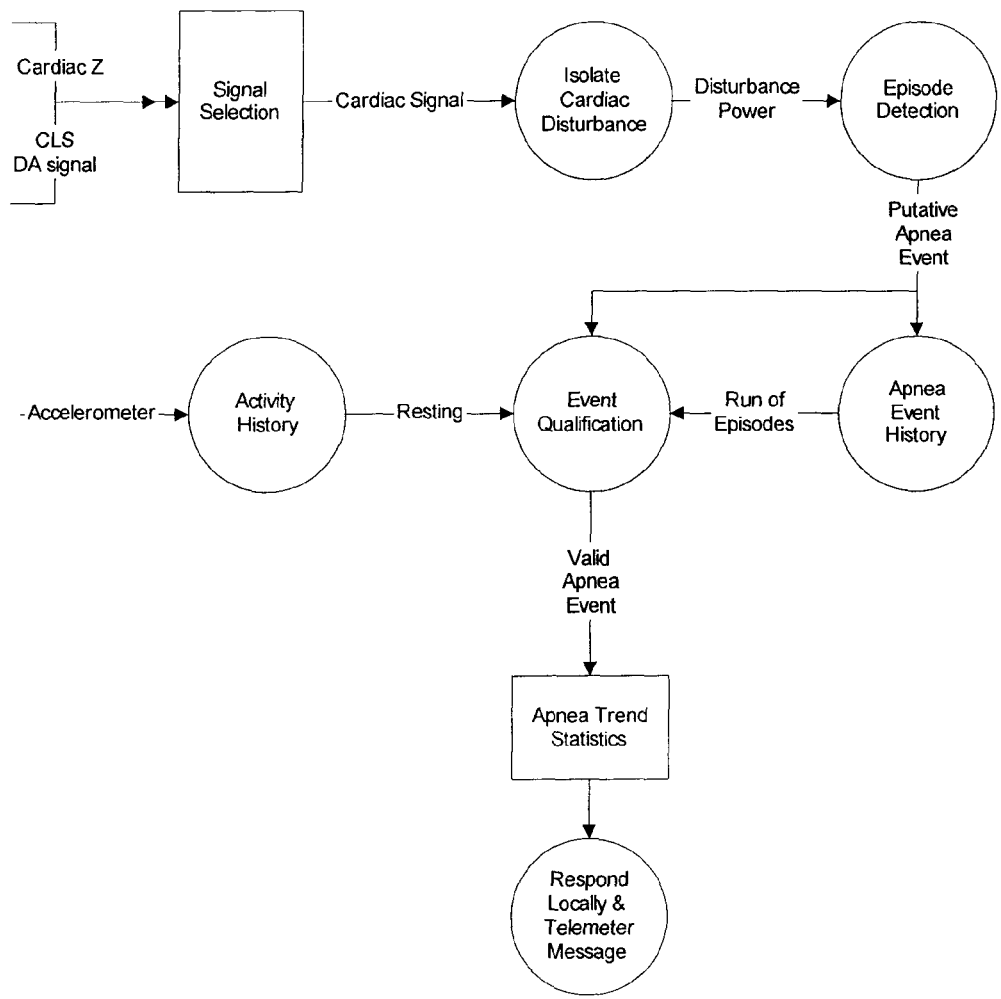
FIG. 5 is a signal processing diagram of the algorithmic processing of impedance data to determine the Sleep Disordered Breathing burden.

Similarly, an impedance measuring unit 74 for measuring a voltage corresponding to a current fed through a body by said constant current source is provided and can be connected to a number of electrodes, although a switch for switching between these configurations is not shown in FIGS. 4 and 5.

As an alternative to constant current source 72 a constant voltage source can be provided. Then, the measuring unit will be adapted to measure a current strength of a current fed through a body by said constant voltage source.

Both constant current source 72 and impedance measurement unit 74 are connected to an impedance value determination unit 76 that is adapted to determine an impedance value for each measuring current pulse delivered by the constant current source 72.

According to the embodiment shown in FIGS. 1 and 2, the measuring unit 74 and the constant current source 72 are both connected to the right ventricular tip electrode 18 and the IMD case electrode 42 for feeding the constant current via these electrodes and measuring the resulting voltage drop over these electrodes.

The embodiment of FIGS. 3 and 4 allows for further impedance measurement configurations.

Further, an impedance measuring control and evaluation unit 78 is provided, that is connected to said impedance measurement unit and that is adapted to evaluate a sequence of consecutive impedance values determined by said impedance measurement unit. Impedance measuring control and evaluation unit 78 comprises a signal generator module (not shown) to construct the intra-cardiac impedance or conductance signal reflecting the time course of the impedance measurement unit's output signal and its derivative.

Impedance measuring control and evaluation unit 78 further comprises a filter module (not shown) to filter the intra-cardiac impedance signal. Impedance measuring control and evaluation unit 78 comprises is connected to memory 56 and to telemetry unit 58 to allow for storing of impedance data and further evaluation by an external service center.

FIG. 5 shows the algorithmic data processing as performed by the control unit 54 using the output signal from impedance determination unit 70.

The output signal from impedance determination unit 70 is an impedance signal containing predominately cardiac functional information, such as the closed-loop-stimulation differential area (CLS DA) measurement as disclosed in U.S. Pat. No. 6,405,085, or another intra-cardiac impedance measurement is selected for a primary signal source.

The control unit 54 comprises a signal selection multiplexer (not shown) that isolates the variability in this impedance signal for processing an impedance signal containing predominately cardiac functional information. The variability in this impedance signal is measured and band-pass filtered. The disturbance signal is used to detect a putative apnea event. The putative apnea event is qualified by secondary correlates including the absence of physical activity and the presence of similar events in the recent history.

The episode detection process performed by the control unit 54 is adaptive. The apnea event and its duration is logged in the memory 56 as part of the statistics on the SDB burden. The SDB burden is transmitted to the central service center via the telemetry unit 58. The SDB burden is made available to the device for actions to reduce the cardiac component of the SDB burden.

Eight delta impedance measurements (impedance change measurements) are performed spanning a systole from ~46 ms to ~280 ms following a ventricular activation (ventricular event). Each impedance or conductance change measurement reflects cardiac dynamics. For the purpose of creating an apnea detector, it is sufficient to consider the total resistance or impedance change due to systole. From the eight impedance change measurements, an RV Systolic Impedance Change signal, RV_SIC, is generated by control unit 54. RV_SIC is the sum of the absolute values of the eight measurements obtained during systole. One RV_SIC value is determined for each ventricular contraction.

$$RV\_SIC = \sum_{i=1}^{8} |\Delta Z_i|$$

Then, control unit 54 generates a Total Active Right Ventricular Impedance signal, TARVI. The Total Active Right Ventricular Impedance, is a measure of the variability in the systolic impedance change and thus, TARVI is a measure of the variability in the RV_SIC signal. For a specific TARVI measurement at time point, $t_n$, TARVI is the standard deviation of:
1) the previous 8 RV_SIC values,
2) the nth RV_SIC value, and
3) the subsequent 8 RV_SIC values.

The value of 8 is used for demonstrative purposes and does not limit the band for isolating the spectral power.

$$TARVI_n = std(RV\_SIC_{n-8} \ldots SR\_SIC_{n+8})$$

The TARVI result is delayed by 8 cardiac cycles. To facilitate computation, the control unit 54 calculates the mean absolute deviation rather than the square root of the variance. The device also normalizes TARVI to a zero mean. The device detects a putative apnea episode by the positive going threshold crossing of the normalized TARVI. The device provides post detection blanking, that is, once an apnea event is detected further detection is paused for an apnea blanking period of (for example) 30 s. Approximately thirty seconds blanking between detected episodes is useful to avoid multiple detections for a single crossing. The threshold crossing is usually coincident with the end of an apnea event. The detection threshold is automatically adjusted.

In the preferred embodiment, a putative apnea episode is accepted if both of the following criteria are met:
1) the absence of activity on the accelerometer circuit for a suitable resting period and
2) a prior putative apnea event has occurred within 2 minutes.

| Definition of Apnea Detection Contingency Table | | | |
| --- | --- | --- | --- |
| | Apnea present | Breathing present | total |
| Apnea detected | true positive breathing detected and apnea was present | False positive breathing detected but apnea was present | Total apnea |
| Breathing detected | False negative breathing detected but apnea was present | true negative breathing detected and apnea was present | Total breathing |

Sensitivity:
ΣTrue Positives/(ΣTrue Positives+ΣFalse Negatives)
A high sensitivity means if apnea is not detected, then the patient probably has a low Apnea/Hypopnea Index (AHI).

Specificity:
ΣTrue Negatives/(ΣTrue Negatives+ΣFalse Positives)
A high specificity means if apnea is detected, then the patient probably has an elevated AHI.

In order to be able to treat SDB, a nerve stimulation stage (not shown) is provided with the IMD and is connected to control unit 54. The nerve stimulation stage is adapted to generate electric stimulation pulses for nerve stimulation. It is connected to or can be connected to a nerve stimulation electrode for stimulation of, for example, inhibitory nerves targeting the heart. The control unit 54 is adapted to trigger the nerve stimulation stage upon detection of SDB to stimulate the inhibitory nerves targeting the heart to reduce the cardiac excitability.

Alternatively, control unit 54 may be adapted to modify the heart rate by stimulation of the heart in order to reduce the cardiac excitability.

Although an exemplary embodiment of the present invention has been shown and described, it should be apparent to those of ordinary skill that a number of changes and modifications to the invention may be made without departing from the spirit and scope of the invention. In particular, it is possible to chose other electrode configurations for impedance determination based on the electrode configurations available for a particular device. This invention can readily be adapted to a number of different kinds of implantable medical devices by following the present teachings. All such changes, modifications and alterations should therefore be recognized as falling within the scope of the present invention.

What is claimed is:

1. A heart monitoring system for monitoring at least a ventricle of a heart, the heart monitoring system comprising:
   a. a ventricular sensing stage connected or being connectable to an electrode for picking up electric potentials inside at least a ventricle of a heart, the sensing stage sensing an expansion or a contraction of a ventricular myocardium,
   b. an activity sensor unit determining an activity signal reflecting a patient's physical activity,
   c. a ventricular impedance or conductance measuring module connected or being connectable to an electrode, the impedance or conductance measuring module including:
      (1) a current source unit providing a sub-threshold excitation current to the myocardium, and
      (2) a voltage measurement unit measuring a resulting voltage on the electrode at the myocardium,
   d. a signal generator module connected to the current source unit and the voltage measurement unit, the signal generator module being configured to construct an intra-cardiac impedance or conductance signal representing impedance and/or conductance:
      (1) of the myocardium of the heart, and
      (2) excluding thoracic impedance and/or conductance arising from breathing,
   e. a filter module filtering the intra-cardiac impedance or conductance signal,
   f. a memory storing a history of intra-cardiac impedance or conductance signal values,
   g. a control unit connected to the memory, the ventricular sensing stage, the activity sensor unit and to the ventricular impedance or conductance measuring module, the control unit being configured to:
      (1) derive an intra-cardiac impedance or conductance change over a preset sample time interval,
      (2) determine a variability in the intra-cardiac impedance or conductance change over a number of cardiac cycles,
      (3) compare:
         (a) the variability in the intra-cardiac impedance or conductance change, and
         (b) the activity signal,
         with threshold values and recent values,
      (4) use the comparison to determine if an episode of sleep disturbed breathing is present, and
      (5) if sleep disturbed breathing is present, log the sleep disturbed breathing episode in the memory.

2. The heart monitoring system of claim 1 wherein the control unit is configured to automatically:
   a. select a baseline impedance signal, and
   b. determine the intra-cardiac impedance or conductance change from the baseline impedance signal,
   when generating the comparison.

3. The heart monitoring system of claim 1 wherein the heart monitoring system is adapted to identify sequences of sleep disturbed breathing episodes and measure the sequence duration for each identified sequence.

4. The heart monitoring system of claim 3 wherein the control unit accumulates a sleep disturbed breathing burden, the sleep disturbed breathing burden being the sum of sequence durations of sleep disturbed breathing episodes over an interval of time.

5. The heart monitoring system of claim 4 wherein the control unit is adapted to initiate wireless transmission of a message containing data characterizing the sleep disturbed breathing burden to an external device.

6. The heart monitoring system of claim 1 wherein the heart monitoring system detects putative apnea events, the detection being at least partially determined by:
   a. a degree of physical activity indicated by the activity sensor unit, and
   b. the presence of any recent sleep disturbed breathing episodes.

7. The heart stimulating system according to claim 6 wherein the control unit modifies a heart rate upon detection of a putative apnea event.

8. The heart monitoring system of claim 6 wherein the control unit modifies a cardiac afferent neural signal upon detection of a putative apnea event.

9. The heart monitoring system of claim 8 wherein the control unit is connected to a nerve stimulation stage, the nerve stimulation stage stimulating inhibitory nerves in communication with the heart.

10. The heart monitoring system of claim 1 wherein the activity sensor unit includes an accelerometer.

11. The heart monitoring system of claim 1 wherein the heart monitoring system is at least partially within an implantable medical device.

12. The heart monitoring system of claim 11 wherein the implantable medical device includes one or more of a heart stimulator and a cardioverter/defibrillator.

13. The heart monitoring system of claim 1 wherein the preset sample time interval over which the intra-cardiac impedance or conductance change is derived occurs over only a portion of a cardiac cycle.

14. The heart monitoring system of claim 13 wherein the intra-cardiac impedance or conductance change includes changes in intra-cardiac impedance or conductance between successive cardiac cycles.

15. The heart monitoring system of claim 14 wherein the variability in the intra-cardiac impedance or conductance change over a number of cardiac cycles is determined by a sum of the absolute values of the changes in intra-cardiac impedance or conductance.

16. The heart monitoring system of claim 1 wherein the preset sample time interval over which the intra-cardiac impedance or conductance change is derived occurs over only a systole.

17. A heart monitoring system for monitoring at least a portion of a patient's heart, the heart monitoring system including:
   a. an activity sensor generating an activity signal representative of a patient's physical activity;
   b. a ventricular current source unit providing an excitation current to the myocardium of the heart;
   c. a ventricular voltage measurement unit measuring a voltage at the myocardium resulting from the excitation current;
   d. a signal generator in communication with the ventricular current source unit and the ventricular voltage measurement unit, the signal generator being configured to generate an intra-cardiac signal reflecting an impedance and/or conductance:
(1) of the myocardium of the heart, and
(2) excluding impedance and/or conductance occurring from breathing,
e. a control unit configured to:
(1) determine changes in
(a) the activity signal, and
(b) the intra-cardiac signal,
over time, and
(2) generate a sleep disordered breathing signal indicative of the presence of sleep disturbed breathing in dependence on the changes.

18. The heart monitoring system of claim 17 wherein the activity sensor includes an accelerometer.

19. The heart monitoring system of claim 17 further comprising a sensing stage in communication with the control unit, the sensing stage sensing expansion and/or contraction of the heart.

20. The heart monitoring system of claim 17 further comprising a wireless transmitter in communication with the control unit, wherein the wireless transmitter transmits the sleep disordered breathing signal.

21. The heart monitoring system of claim 17 wherein at least substantially the entirety of the heart monitoring system is implanted within a human body.

22. The heart monitoring system of claim 17 further including a heart rate modification electrode in communication with the control unit, wherein the heart rate modification electrode delivers electrical stimulation to the heart in dependence on the presence of sleep disturbed breathing.

23. The heart monitoring system of claim 17 further including a neural modification electrode in communication with the control unit, wherein the neural modification electrode delivers electrical stimulation to the nervous system in dependence on the presence of sleep disturbed breathing.

24. The heart monitoring system of claim 17 wherein the intra-cardiac signal reflects the impedance and/or conductance of the myocardium over portions of several cardiac cycles.

25. The heart monitoring system of claim 17 wherein the control unit determines changes in the impedance and/or conductance of the myocardium between successive cardiac cycles.

26. The heart monitoring system of claim 25 wherein the the control unit determines a sum of absolute values of the determined changes.

27. The heart monitoring system of claim 17 wherein the intra-cardiac signal reflects the impedance and/or conductance of the myocardium during a systole of the cardiac cycle.

28. A heart monitoring system for monitoring at least a portion of a patient's heart, the heart monitoring system including:
a. a signal generator configured to generate an intra-cardiac signal representative of myocardial impedance and/or conductance, excluding impedance and/or conductance from breathing,
b. a control unit configured to:
(1) determine changes in the intra-cardiac signal over time, and
(2) monitor the changes for a characteristic of sleep disturbed breathing, and
(3) when the characteristic is present, generate a signal indicative of the presence of sleep disturbed breathing.

29. A method for monitoring a patient's heart, the method including the steps of:
a. generating an intra-cardiac signal representative of myocardial impedance and/or conductance, the intra-cardiac signal excluding impedance and/or conductance from breathing;
b. determining changes in the intra-cardiac signal over time;
c. monitoring the changes for a characteristic of sleep disturbed breathing; and
d. when the characteristic is present, generating a signal indicative of the presence of sleep disturbed breathing,
the foregoing steps being performed at least partially within an implantable medical device.

30. The method of claim 29 further including the step of administering electrical stimulation to the patient at least partially in response to the signal indicative of the presence of sleep disturbed breathing.

31. The method of claim 29 further including the step of modifying a heart rate when the characteristic of sleep disturbed breathing is present.

32. The method of claim 29:
a. wherein the signal indicative of the presence of sleep disturbed breathing is generated within the implantable medical device while implanted inside the patient's body;
b. further including the step of wirelessly transmitting data relating to the signal to an external device.

33. The method of claim 29 further including the step of logging instances of sleep disturbed breathing within a memory.

34. The method of claim 29 wherein the changes determined in the intra-cardiac signal over time are determined between portions of successive cardiac cycles.

* * * * *